United States Patent [19]

Hock

[11] Patent Number: 5,753,822
[45] Date of Patent: May 19, 1998

[54] METHOD AND DEVICE FOR DETERMINING THE GREEN TACK OF RUBBER BLENDS

[75] Inventor: Bernd Hock, Gross-Ostheim, Germany

[73] Assignee: Pirelli Reifenwerke GmbH, Brueberg, Germany

[21] Appl. No.: 865,033

[22] Filed: May 29, 1997

[30] Foreign Application Priority Data

Jun. 4, 1996 [DE] Germany ................. 196 22 410.1

[51] Int. Cl.$^6$ ................................................. G01N 3/08
[52] U.S. Cl. ............................... 73/819; 73/860; 73/805
[58] Field of Search ........................... 73/790, 791, 804, 73/805, 818, 819, 824, 856, 860

[56] References Cited

U.S. PATENT DOCUMENTS

| | | | |
|---|---|---|---|
| 3,404,564 | 10/1968 | Rapp | 73/818 |
| 3,847,018 | 11/1974 | Aston | 73/818 |
| 4,552,025 | 11/1985 | Barker et al. | 73/846 |
| 4,572,002 | 2/1986 | Hartel et al. | 73/831 |
| 5,049,057 | 9/1991 | Yamaguchi et al. | |
| 5,524,636 | 6/1996 | Sarvazyan et al. | 73/818 |

FOREIGN PATENT DOCUMENTS 2220374  11/1973  Germany.

Primary Examiner—George M. Dombroske
Assistant Examiner—Max H. Noori
Attorney, Agent, or Firm—Watson Cole Stevens Davis, P.L.L.C.

[57] ABSTRACT

A method and device for determining the green tack of rubber blends. To obtain reliable and reproducible measurement results it is proposed to use two specimens (40') of rubber blends, the green tack of which is to be determined. Each of the specimens (40') comprises a measurement surface area (42) having a convex curvature, with which the specimens (40') are placed one on the other. During a predetermined time the specimens (40') are compressed at a predetermined pressure and subsequently parted from each other at a constant rate to determine the maximum parting force. The curved measurement surface areas (42) are generated by a specimen (40) being placed on the specimen platform (34) of a specimen mount (26, 28). Subsequently an orifice disk (36) is placed on the specimen (40) and locked in place in the compressed condition, for instance, by being firmly bolted in place. Due to the pressure on the orifice disk (36) the specimen (40) is forced therethrough and bulges outwardly through the orifice (38) of the orifice disk (36). Thus, a consistent measurement surface area is employed.

13 Claims, 2 Drawing Sheets

METHOD AND DEVICE FOR DETERMINING THE GREEN TACK OF RUBBER BLENDS

FIELD OF THE INVENTION

The invention relates to a method and device for determining the green tack of rubber blends.

BACKGROUND OF THE INVENTION

The adhesiveness of rubber blends, the so-called green tack, represents a major parameter for the rubber industry. Thus, in tire manufacture, for instance, the green tack of the semi-finished products is the deciding factor as to whether the rubber blends in each case may be combined at all. Accordingly, determining the green tack is basic to quality assurance.

In this respect the green tack of rubber blends is determined by measurements made manually or powered. In manual measurement two test strips of the rubber blends concerned are pressed together manually and then parted. The parting or peeling force experienced subjectively by the person carrying out the measurement is thereby evaluated and scaled according to a grading system. In this method the green tack is thus determined by comparison with values gained subjectively from experience. In the powered method of measurement a strip of polyester film (PE film) is rolled by a roller onto a test specimen of the rubber blend or semi-finished product and then peeled off horizontally by a dynamometer. Although in this method for determining the green tack a force is determined which is objectively measurable, as is necessary to release the film from the rubber blend, the boundary conditions of such a powered measurement fail to be suitable in assuring that the results of the measurement can be reliably reproduced. This makes it highly unlikely that agreeing measured values are achieved when the powered measurement is done by different persons. Accordingly the reliability of such values is poor.

SUMMARY OF THE INVENTION

The invention is based on an object of providing a method for determining the green tack of rubber blends which ensures high reproducibility and thus reliable measurement values. The invention is furthermore based on an object of providing a device for determining the green tack of rubber blends which permits reliable determination of measurement values with high reproducibility.

To achieve these objects, a method is proposed in accordance with the invention for determining the green tack of rubber blends. In particular the invention relates to a method for determining the green tack of rubber blends comprising the following steps:

A. providing two specimens (40') of one or differing rubber blends, the green tack of which is to be determined, each of the specimens (40') comprising a measurement surface area (42) of a predetermined size and having a convex curvature, B. locating the measurement surface areas (42) of the two specimens (40') flush one on the other, C. subjecting the measurement surface areas (42) placed one on the other to a predetermined pressure for a predetermined period of time, D. parting the two specimens (40') by peeling at a constant rate and determining the maximum parting force as a measure of the green tack.

For convenience, and not as a limitation, reference numerals to elements in figures of the present application are indicated in this Summary in parenthesis.

The invention is based on the knowledge that realizing a reproducible determination of green tack necessitates the existence of boundary conditions which are objectively duplicatable. This is achieved, on the one hand, by predetermining the parameters decisive to pressing together the rubber blends, the green tack of which is to be determined. More particularly, predetermined parameters include the value of the pressure and the length of the time duration, during which this pressure is exerted, as well as the size of the measurement surface areas sticking to each other. However, the salient aspect of the invention is based on the fact that the measurement surface areas of the rubber specimens to be pressed together exhibit a convex curvature (bulge).

It has namely been discovered that for achieving reproducible results in measurement it is also necessary to eliminate measurement errors stemming from effects which occur during pressing together and subsequent parting of rubber specimens and which are capable of influencing the measurement results. Involved in this respect, more particularly, are suction effects between the measurement surface areas which result in the maximum parting or peel force measured not having a linear relationship to the measured surface area. By providing convex curved measurement surface areas in accordance with the invention the aforementioned suction effects during pressing together of two such measurement surface areas are avoided. Thus, maximum peel force measured in parting the two rubber specimens is a direct measure of the green tack of the rubber blends involved which is reproducible to a high degree.

In one advantageous embodiment of the invention the above-listed "step A" further includes the following steps to achieve the above-listed "convex curvature (buldge)":

inserting each provided specimen (40) in a specimen mount (26, 28), applying an orifice disk to each specimen (40), and defining the orifice disk (36) such that a portion the specimen (40) is forced therethrough to bulge outwardly from the orifice (38) of the orifice disk (36).

In this embodiment the convex curvature of the measurement surface areas of the rubber specimens is achieved by placing an orifice disk of predetermined shape and size on the specimen inserted in a specimen mount and secured, for instance, by being firmly bolted in place. Due to the orifice disk being pressed onto the specimen the rubber blend is forced through the orifice, forming an outwards curvature (bulge). The portion of the rubber specimen protruding from the orifice of the orifice disk thus represents the measurement surface area of the specimen.

To assure best possible reproducibility, an orifice film is inserted between the two measurement surface areas prior to the rubber blends being pressed together. As a result of providing the orifice film, a particularly good consistency of the tack surface area between the two rubber blends is achieved.

Further advantageous embodiments of the method in accordance with the invention are described in this specification. For example, the method may include the step of providing a force/time graph plotting device.

In a further aspect of the object concerned, a device for performing the method of the present invention of determining the green tack of rubber blends in accordance with the invention is proposed. The device comprises the following features:

two specimen mounts (26, 28) each incorporating an orifice disk (36) for mounting a specimen (40) of a rubber blend and to define a respective measurement surface area (42) for each specimen (40), wherein the green tack of the specimens (40) is to be determined, a combination push/pull dynamometer (20, 22) having a push/pull gauge (20) for measuring the force of pressure or tension applied to compress, and the force of pressure or tension applied to part, the measurement surface areas (42) respectively, wherein the specimen mounts (26, 28) are aligned and located to oppose each other and are each configured to produce the measurement surface (42) to have a convex curved surface by placing and tightening the respective orifice disk (36) on the respective specimen (40) in the respective mount (26, 28), the specimen mounts (26, 28) being located in the combination push/pull dynamometer (20, 22) to have the measurement surfaces (42) oppose each other, the specimen mounts (26, 28) being vertically adjustable relative to each other to compress and part the measurement surface areas (42) respectively in the combination push/pull dynamometer (20, 22) having the push/pull gauge (20).

A preferred embodiment of the device also includes a force/time graph plotting means.

This device is particularly suitable for implementing the method in accordance with the invention. This device is simple and inexpensive to produce and permits the production of rubber blend specimens in accordance with the invention having a convex curved measurement surface area, the size of which is reliably consistent and permitting good reproducibility.

BRIEF DESCRIPTION OF THE DRAWINGS

The invention will now be described in detail by way of an example embodiment with reference to the drawings in which.

DETAILED DESCRIPTION OF THE PREFERRED EMBODIMENTS

Figure 1:
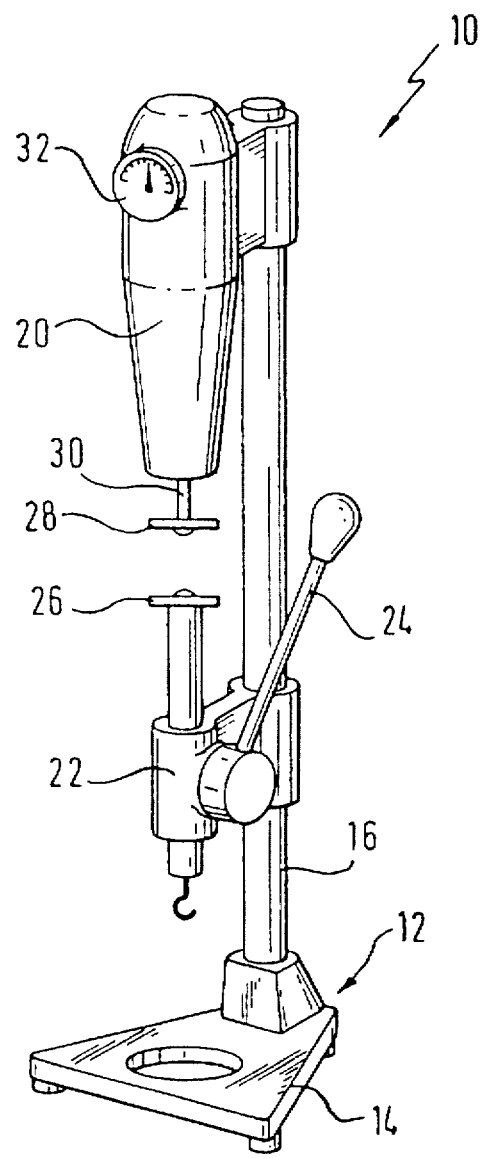
FIG. 1 is a perspective schematic illustration of a device in accordance with the invention for determining the green tack of rubber blends.

FIG. 1 shows a device 10 in accordance with the invention for determining the green tack of rubber blends in a perspective view. The device 10 comprises a test stand 12 with a base 14 and a round-section rod 16 extending vertically upwards from the base 14. The round-section rod 16 serves to mount a combination push/pull dynamometer 20, 22 comprising a push/pull gauge 20 in the vicinity of the upper end of the round-section rod 16. Disposed below the push/pull gauge 20 is a counter-piece 22. This counter-piece 22 is adjustable up and down along the round-section rod 16 by means of a pull lever 24. In its resting position the counter-piece 22 is located spaced away from the push/pull gauge 20. The pull lever 24 is preferably a pull lever having a non-delayed effect for fast measurements.

The push/pull gauge 20, 22 comprises further a lower and upper specimen mount 26, 28 disposed facing each other concentrically. The lower specimen mount 26 is assigned to the counter-piece 22 to which it is secured. The upper specimen mount 28 is assigned to the push/pull gauge 20, it being connected to the measuring linkage of the push/pull gauge 20.

By actuating the pull lever 24, the counter-piece 22 can be upwardly adjusted along the round-section rod 16 until the lower specimen mount 26 of the counter-piece comes up against and impacts the upper specimen mount 28 of the push/pull gauge 20. Depending on the force with which the pull lever 24 is actuated, the upper specimen mount 28 is urged with the measuring linkage 30 more or less upwards due to impact with the lower specimen mount 26. This deflection of the upper specimen mount 28 and measuring linkage 30 is converted in the push/pull gauge 20 into an indication of force by a meter instrument 32.

When the pull lever 24 is returned back and urged past its starting position the lower specimen mount 26 and together therewith the upper specimen mount 28 descends. Since the rubber blends applied as specimens to the specimen mounts 26, 28 tack to each other, the upper specimen mount 28 is deflected downwards beyond its resting position. This deflection occurs until the two rubber blends are parted from each other and is indicated as a pull force on the meter instrument 32.

Figure 2:
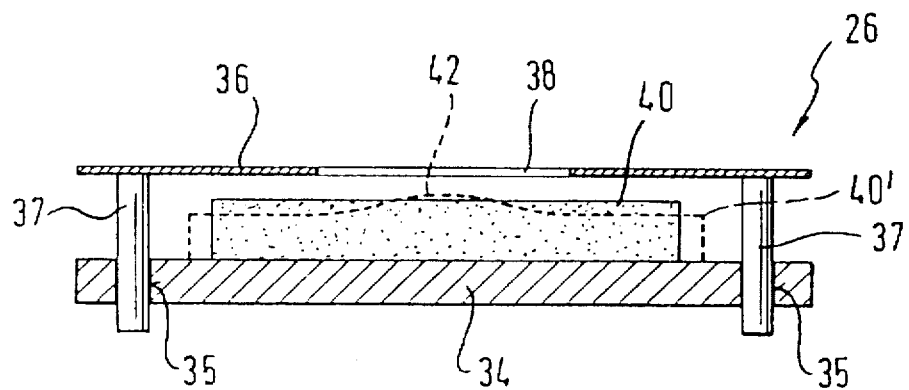
FIG. 2 is a side section illustration of a specimen mount including orifice disk and inserted blend specimen for use in the device as shown in FIG. 1.

For explanation by way of an example, FIG. 2 is a side section illustration of the lower specimen mount 26 of the combination push/pull dynamometer 12 shown in FIG. 1. The upper specimen mount 28 is configured substantially the same as the lower specimen mount 26. Thus, each of the upper and lower mounts comprise an essentially flat rectangular or square specimen platform 34 on which a specimen 40 of a rubber blend, the green tack of which needs to be determined, can be arranged. Provided above the specimen 40 is an orifice disk 36 having an orifice 38 in the middle. The orifice disk 36 is provided with several vertically protruding pins 37 arranged in its edge portion. By means of these pins the orifice disk can be inserted in drilled holes 35 provided accordingly in the specimen platform 34 for orientation and guidance purposes. It is of advantage when four pins 37 are provided, one in each corner portion of the orifice disk 36. The pins 37 and the drilled holes 35 are dimensioned so that the pins 37 can be snugly inserted in the drilled holes 35 and guided therein.

The specimen 40 is arranged on the specimen platform so that the orifice 38 of the orifice disk 36 is completely filled and extends sufficiently far beyond the edges of the orifice 38 on all sides. The orifice disk 36 is then lowered and forced against the specimen 40 so that the specimen is forced through. In the region of the orifice 38 a bulge 42 materializes from the specimen 40 being pressed through. In this held-down condition the orifice disk 36 is located in place, for instance, by means of wing nuts (not shown) which may be mounted on a screw thread provided on the pins 37 and tightened. Due to the orifice disk 36 being pressed down, the specimen 40 assumes the shape 40' indicated dotted in FIG. 2.

The feature essential to the invention consists of the convex curvature (bulging) of the specimen 40' produced by the existence of the orifice 38, the orifice disk 36 being pressed down so far that the bulge protrudes upwards through the orifice 38 beyond the orifice disk 36 and may serve as the measurement surface area 42 of the specimen 40'.

Figure 3:
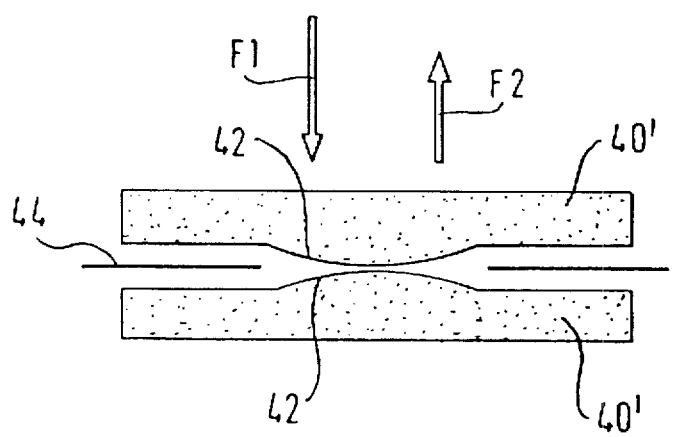
FIG. 3 illustrates how the convex curved measurement surface areas in accordance with the invention are pressed together with an orifice film interposed.

FIG. 3 illustrates the principle of the measurement forming the basis of the invention by pressing two specimens 40' on each other and subsequently parting them, each of which has a bulging measurement surface area 42 in accordance with the invention. In this arrangement the bulge of the measurement surface area 42 may have been produced, for example, by ways and means as explained above. To simplify the illustration, FIG. 3 merely depicts the specimens of the rubber blends without the specimen mount in each case.

Each of the two specimens 40' consists of a rubber blend, the green tack of which is to be determined. In this arrangement the rubber blend may be identical for the two specimens, it also being possible, however, to gauge two different rubber blends.

For implementing the method in accordance with the invention, the specimens 40' are arranged so that their convex curved measurement surface areas 42 face each other opposingly. The two specimens 40' are then pressed against each other for a specific time with a specific force. The force of this pressure is indicated by the downwards directed arrow F1 in FIG. 3. Subsequently the two specimens 40' are pulled contrary to the pressure force up to a maximum parting force so that they release from each other in FIG. 1. This maximum parting force is indicated by the upwards directed arrow F2 in FIG. 3. As a rule the maximum parting force is smaller than the pressure force with which the two specimens 40' were pressed together, this being the reason why the arrow F2 is shorter than the arrow F1.

Due to the convex curvature of the measurement surface areas 42 in accordance with the invention, measurement errors in determining the green tack of rubber blends are prevented which in the case of conventional flat specimens are caused by suction effects. In accordance with the invention, reliable and reproducible measurement results are attained. To even further improve the reproducibility of the measurement, an orifice film 44 may be further provided between the two specimens 40'. The orifice film 44 further contributes towards maintaining the actual measurement surface area constant, i.e. the surface area via which the two bulging measurement surface areas 42 actually tack to each other. One suitable material for the orifice film 44 is, for example, polyester.

In preparing the specimens it is to be noted to ensure a good reproducibility, that the specimens are cooled to room temperature and that neither dust, nor dirt or moisture is present on the bulging measurement surface area. More particularly the measurement surface areas 42 should not be touched by hand since grease from the skin transferred on touching results in measurement errors. Where necessary, the measurement surface areas are to be covered with a smooth film.

So that a good curvature of the measurement surface area can be achieved, the specimens should be neither too thick nor too thin. Specimens which are too thick are thus further cleaved, the measurement surface area thereof needing to be covered with a smooth film during cleaving. Specimens which are too thin are doubled on a backing material, for instance, on hide. Fabric is advantageously measured crisscross, textile fabric is doubled on hide and steel cord is not doubled. Apexes are doubled on themselves so that a equal specimen thickness materializes.

It has been demonstrated to be advantageous for the rubber blend specimens to have a thickness of maximum 15 mm for a surface area of roughly 40×40 sq.mm. The orifice disk should be sufficiently thin so that the bulge of the specimen is able to protrude through the orifice above the orifice disk with no problem, while the other side is sufficiently stable so that no deformations occur. The thickness of the orifice disk amounts to roughly 1.5 mm, the orifice in the orifice disk being substantially circular and having a diameter of 1.5 cm, corresponding to a measurement surface area of approx 1.77 sq.cm.

For implementing the measurement, the meter is set to zero and by means of the pull lever the pressure is jumped to 50N abruptly, i.e. within roughly 1 second. This pressure of 50N is maintained for 10 seconds before being dumped to zero, again within roughly 1 second and then pulled somewhat slower (approx. 2 seconds) up to maximum parting force. Experience has shown in practice that the aforementioned values, for the contact pressure and the contact pressure, pull and holding times, are well maintainable. Of course, values other than these may also be provided for. However, it win be appreciated that these other values should relatively constant, i.e., not be changed, over a lengthy period (sufficient for measuring a desired number of samples) to ensure comparable results in measuring the green tack of rubber blends. The green tack according to the HOCK tack force method then corresponds to the measured maximum parting force at which the specimen surface areas release from each other. To better demonstrate the measuring procedure it is of advantage to connect a force/time plot recording means (not shown) to the combination push/pull dynamometer.

More particularly, an embodiment of the device in accordance with the invention replaces the manual part of the device by an automatic unit with a spindle drive (not shown). In this arrangement, with the automatic unit, the prescribed contact pressure, parting and holding times can be exactly maintained so that ever better accuracy and reproducibility of the measurement values is achieved.

EXAMPLES

The high reproducibility of the measurement values achieved in accordance with the invention was documented by testing in which four test persons achieved the results as listed in the following for three measurements carried out in each case on identical specimens. Also indicated are the accuracies of the measurements and the standard departures.

| Test Person | a | b | c | d |
| --- | --- | --- | --- | --- |
| Value 1 [N/1.8 sq.cm] | 40 | 42 | 39 | 41 |
| Value 2 [N/1.8 sq.cm] | 43 | 39 | 43 | 40 |
| Value 3 [N/1.8 sq.cm] | 39 | 40 | 42 | 42 |
| Average Value | 40.7 | 40.3 | 41.2 | 41.0 |
| | Indiv. measurements | | | Average |
| No. of results | 12 | | | 4 |
| Average, total | 40.8 | | | 40.8 |
| Confidence range (90%) | ±0.8 | | | ±0.5 |
| Standard departure | 1.5 | | | 0.4 |

In view of the high resolution documented for these tests even an individual measurement in accordance with the invention method produces a very good indication. To obtain a reliable result it is good practice to form the average value from three measurements.

What is claimed is:

1. A method for determining the green tack of rubber blends comprising the following steps:

A. providing two specimens (40') of one or differing rubber blends, the green tack of which is to be determined, each of said specimens (40') comprising a measurement surface area (42) of a predetermined size and having a convex curvature, B. locating said measurement surface areas (42) of said two specimens (40') flush one on the other, C. subjecting said measurement surface areas (42) placed one on the other to a predetermined pressure for a predetermined period of time, and D. parting said two specimens (40') by peeling at a constant rate and determining the maximum parting force as a measure of the green tack.

2. The method as set forth in claim 1, wherein said step A further comprises:

inserting each said provided specimen (40) in a specimen mount (26, 28), applying an orifice disk to each said specimen (40), and defining said orifice disk (36) such that a portion of said specimen (40) is forced therethrough to bulge outwardly from the orifice (38) of said orifice disk (36).

3. The method as set forth in claim 1, wherein for maintaining said measurement surface area (42) constant an orifice film (44), having an orifice which defines the measurement surface area, is provided between said specimens (40') prior to placement of said specimens (40') flush one on the other.

4. The method as set forth in claim 2, wherein for maintaining said measurement surface area (42) constant an orifice film (44), having an orifice which defines the measurement surface area, is provided between said specimens (40') prior to placement of said specimens (40') flush one on the other.

5. The method as set forth in claim 1, wherein said measurement surface area (42) has a substantially circular perimeter.

6. The method as set forth in claim 5, wherein the diameter of said measurement surface area (42) is about 1.5 cm.

7. The method as set forth in claim 1, wherein said measurement surface areas (42) are subjected to a pressure of about 50N for about 10 seconds.

8. The method as set forth in claim 1, wherein a combination push/pull dynamometer (20, 22) is provided for controlling and measuring the force in pressure and tension.

9. The method as set forth in claim 3, wherein a combination push/pull dynamometer (20, 22) is provided for controlling and measuring the force in pressure and tension.

10. The method as set forth in claim 8, wherein a plotter for plotting a force/time graph is provided.

11. A device for determining green tack of rubber blends, in accordance with the method as set forth in claim 1, comprising two specimen mounts (26, 28) each incorporating an orifice disk (36) for mounting a specimen (40) of a rubber blend and to define a respective measurement surface area (42) for each specimen (40), wherein the green tack of the specimens (40) is to be determined, a combination push/pull dynamometer (20, 22) having a push/pull gauge (20) for measuring the force of pressure or tension applied to compress, and the force of pressure or tension applied to part, said measurement surface areas (42) respectively, wherein said specimen mounts (26, 28) are aligned and located to oppose each other and are each configured to produce the measurement surface (42) to have a convex curved surface by placing and tightening said respective orifice disk (36) on said respective specimen (40) in said respective mount (26, 28), said specimen mounts (26, 28) being located in said combination push/pull dynamometer (20, 22) to have said measurement surfaces (42) oppose each other, said specimen mounts (26, 28) being vertically adjustable relative to each other to compress and part said measurement surface areas (42) respectively in said combination push/pull dynamometer (20, 22) having said push/pull gauge (20).

12. The device as set forth in claim 11, further comprising a force/time graph plotter for plotting said force of said pressure or tension applied to compress and part said measurement surface areas (42) and the time for measuring such pressure or tension.

13. The device as set forth in claim 12, wherein said measurement surface area (42) has a substantially circular perimeter.

* * * * *